United States Patent
Borruto et al.

(10) Patent No.: US 7,896,925 B2
(45) Date of Patent: Mar. 1, 2011

(54) HIP PROSTHESIS AND DESIGNING METHOD THEREOF

(75) Inventors: Adelina Teresa Maria Borruto, Rome (IT); Luigi Marrelli, Rome (IT)

(73) Assignee: Universita degli Studi di Roma, Rome (IT)

( * ) Notice: Subject to any disclaimer, the term of this patent is extended or adjusted under 35 U.S.C. 154(b) by 122 days.

(21) Appl. No.: 10/493,285

(22) PCT Filed: Feb. 14, 2002

(86) PCT No.: PCT/IT02/00086
§ 371 (c)(1),
(2), (4) Date: Sep. 28, 2004

(87) PCT Pub. No.: WO03/035129
PCT Pub. Date: May 1, 2003

(65) Prior Publication Data
US 2005/0021149 A1    Jan. 27, 2005

(30) Foreign Application Priority Data
Oct. 23, 2001   (IT) ............................. RM2001A0628

(51) Int. Cl.
*A61F 2/44*    (2006.01)
(52) U.S. Cl. .................................................... 623/22.15
(58) Field of Classification Search ................ 623/22.15, 623/22.33, 23.3, 23.35, 23.36, 23.55, 23.57–23.59
See application file for complete search history.

(56) References Cited

U.S. PATENT DOCUMENTS

| | | | | |
|---|---|---|---|---|
| 3,992,725 A * | 11/1976 | Homsy | ........................ | 424/423 |
| 4,808,186 A * | 2/1989 | Smith | ........................ | 623/23.33 |
| 4,963,151 A * | 10/1990 | Ducheyne et al. | ......... | 623/23.62 |
| 5,100,736 A * | 3/1992 | London et al. | ................ | 428/549 |
| 5,169,597 A * | 12/1992 | Davidson et al. | ........... | 428/613 |
| 5,549,700 A * | 8/1996 | Graham et al. | ............. | 623/22.14 |
| 5,571,193 A * | 11/1996 | Kampner | ................... | 623/23.57 |
| 5,591,233 A * | 1/1997 | Kelman et al. | ............. | 623/23.51 |
| 5,594,651 A * | 1/1997 | St. Ville | .......................... | 700/98 |
| 5,609,646 A * | 3/1997 | Field et al. | ................. | 623/22.32 |
| 5,707,231 A * | 1/1998 | Watt et al. | .......................... | 433/8 |
| 5,807,407 A * | 9/1998 | England et al. | ............... | 128/898 |
| 5,879,404 A * | 3/1999 | Bateman et al. | ........... | 623/22.21 |
| 5,981,827 A * | 11/1999 | Devlin et al. | ............. | 623/23.51 |
| 6,121,027 A * | 9/2000 | Clapper et al. | ................ | 435/180 |
| 6,193,516 B1 * | 2/2001 | Story | ............................. | 433/173 |
| 6,290,726 B1 * | 9/2001 | Pope et al. | ................. | 623/22.15 |
| 6,299,649 B1 * | 10/2001 | Chang et al. | ............... | 623/23.34 |
| 6,368,350 B1 * | 4/2002 | Erickson et al. | ........... | 623/17.14 |

(Continued)

OTHER PUBLICATIONS

Wang, et al, "Carbon fiber reinforced polyether ether ketone composite as a bearing surface for total hip replacement" Tribology International, vol. 31, No. 11, 1998, pp. 661-667.

(Continued)

*Primary Examiner* — Eduardo C Robert
*Assistant Examiner* — David Comstock
(74) *Attorney, Agent, or Firm* — Leffert Jay & Polglaze, P.A.

(57) ABSTRACT

Hip prosthesis, comprising a first prosthetic body reproducing an acetabular cup and a second prosthetic body reproducing a femoral head and apt to work coupled to the first prosthetic body, wherein the prosthetic bodies have low debris production and different wettability (θ) (FIG. 20A).

3 Claims, 14 Drawing Sheets

U.S. PATENT DOCUMENTS

| | | | | |
|---|---|---|---|---|
| 6,425,922 | B1 * | 7/2002 | Pope et al. | 623/23.11 |
| 6,582,715 | B1 * | 6/2003 | Barry et al. | 424/422 |
| 6,638,311 | B2 * | 10/2003 | Wang et al. | 623/22.32 |
| 6,641,893 | B1 * | 11/2003 | Suresh et al. | 428/105 |
| 6,699,289 | B2 * | 3/2004 | Iannotti et al. | 623/19.13 |
| 6,709,463 | B1 * | 3/2004 | Pope et al. | 623/23.51 |
| 6,989,030 | B1 * | 1/2006 | Ohgushi | 623/16.11 |
| 2003/0125739 | A1 * | 7/2003 | Bagga et al. | 606/61 |
| 2003/0125809 | A1 * | 7/2003 | Iannotti et al. | 623/19.13 |
| 2005/0049716 | A1 * | 3/2005 | Wagener et al. | 623/23.5 |

OTHER PUBLICATIONS

Albert, et al, "Characterization of wear in composite material orthopaedic implants Part II: The Implant/Bone Interface" Bio-Medical Materials and Engineering, vol. 4, No. 3, 1994, pp. 199-211.

Polineni, et al, "Characterization of Carbon Fiber-Reinforced PEEK Composite for Use as a Bearing Material in Total Hip Replacements" Alternative Bearing Surfaces in Total Joint Replacement, ASTM STP No. 1346, J.J. Jacobs and T.L Craig, Eds., American Society for Testing and Materials, 1998, pp. 266-273.

* cited by examiner

HIP PROSTHESIS AND DESIGNING METHOD THEREOF

FIELD OF INVENTION

The present invention relates to a hip prosthesis and to a designing method thereof. In particular, it relates to a prosthesis comprising a first prosthetic body reproducing an acetabular cup and a second prosthetic body reproducing a femoral head and apt to be coupled to said first prosthetic body.

BACKGROUND OF THE INVENTION

The hip joint has been prosthesized for more than forty years by prosthetic bodies apt to reproduce the coupling between the femoral head and the acetabular cup. These bodies work in an environment encapsulated by the so-called sinovial membrane, which contains a viscous liquid lubricant consisting of plasma, water, salts and hyaluronic acid, called sinovial liquid, apt to ease the sliding of the contacting articular surfaces. Therefore, the relative motion of the latter takes place under aqueous lubrication conditions.

In the normal natural biological system, the friction coefficient between the articular surfaces is usually comprised in a range of values of about 0.005 to 0.025. However, notwithstanding the intensive research in the field, the current prosthetic systems fail to reproduce the performances of the natural system, due to the difficulties of ensuring the setting up of a supporting and stable meatus of sinovial liquid between the prosthetic bodies.

The main problem is that of the wear detritus, often referred to as 'debris', which are one of the main causes for long-term failure of the orthopedic prostheses in general and of the hip prostheses in particular. In fact, debris can get stuck between the two prosthetic bodies, favoring the three-body wear mechanism, or deposit onto the femoral surface near to the prosthetic stem.

This problem is particularly felt just in the case of the prosthetic systems to date most widely adopted, which employ high-molecular weight polyethylene, often indicated with the acronym UHMWPE, for the manufacture of the acetabular cup and of a Chromium-Cobalt (CoCr) alloy, of AISI 316 steel or of a ceramics material for the manufacture of the femoral head. In fact, polyethylene, being the softer material of the coupling, tends to form debris which accumulate in correspondence of the prosthetic stem, so inducing macrophages to migrate thereat, i.e. causing a reaction by the organism which tends to eliminate the debris as extraneous particles. Where the polyethylene debris have relevant dimensions, the macrophages aggregate, forming polynucleated giant cells. If, as it often happens, the macrophages fail to eliminate the debris as the latter are too much and/or too large, an inflammatory process sets up. Moreover, the aggregated macrophages induce the production of substances activating the osteoclastic reaction and therefore the degradation of the bone tissue at the proximal region of the stem. Apparently, these circumstances concur to modify the distribution of the mechanical load onto the prosthesis, unbalancing it, with a consequent danger of mobilizing the latter.

Examination of explanted hip prostheses suggested that the debris problem could be almost completely solved by the use of a coupling between prosthetic bodies both made of ceramics. However, the latter material, although not producing debris, causes an excessive rigidity of the prosthetic system, the bodies of which will scarcely be able to adjust their mutual location after the implant.

The technical problem underlying the present invention is to provide a hip prosthesis and designing method thereof which allow to overcome the drawbacks hereto mentioned with reference to the known art.

This problem is solved by a hip prosthesis, comprising a first prosthetic body reproducing an acetabular cup and a second prosthetic body reproducing a femoral head and apt to be coupled to said first prosthetic body, characterized in that said prosthetic bodies have low debris production and in that said first prosthetic body has a wettability substantially different from that of said second prosthetic body.

According to the same inventive concept, the present invention further relates to a designing method of a hip prosthesis comprising two prosthetic bodies reproducing an acetabular cup and a femoral head, respectively, characterized in that it provides that said prosthetic bodies have a low debris production and a substantially different wettability.

As it will be made apparent from the description which follows, by "substantially different wettability" it is meant that the two prosthetic bodies must have appreciably different wettability properties, e.g. having one an essentially hydrophilic and the other one an essentially hydrophobic behavior, or the one a slightly hydrophilic and the other one a markedly hydrophobic behavior, or vice versa, and so on. In this condition, a lubricated system ensues which, as such, does not produce debris.

The present invention provides several relevant advantages. The main advantage lies in that said opposite wettability of the prosthetic bodies enables the setting up of a markedly stable supporting meatus therebetween.

BRIEF DESCRIPTION OF THE DRAWINGS

Other advantages, features and the modes of employ of the present invention will be made apparent in the following detailed description of some embodiments thereof, given by way of example and without limitative purposes. Reference will be made to the Figures of the attached drawings, wherein.

DETAILED DESCRIPTION

Figure 1:
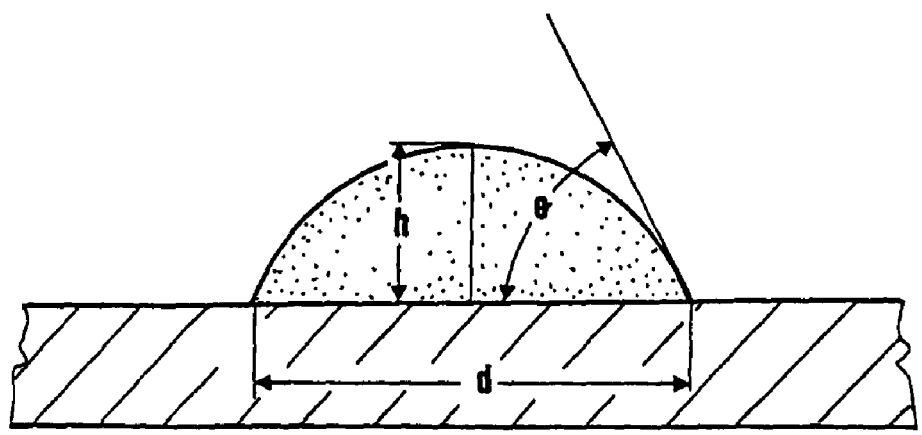
FIG. 1 schematically shows the modes for carrying out an exemplary wettability measurement, i.e. a measurement of the so-called "angle of attack"

As it will be detailed hereinafter, a battery of experimental tests apt to simulate the behaviour in use of specific couplings between prosthetic bodies made of various materials, in particular both polymeric and metallic materials, was carried out. These tests were aimed at evaluating the tribological performances of such specific couplings under aqueous lubrication conditions.

Test Materials

Experimental tests were carried out by the so-called "pin-on-disc" technique, using a commercial METROCOM tribometer. In particular, pins having the shape of a cylinder with a spherical tip (base) were employed.

The following Table 1 summarizes the group of tested couplings. The involved materials have been indicated by the currently adopted technical-commercial references, and they will be cited by such reference in the following.

TABLE 1

CHART OF TESTED COUPLINGS

|    | Disc | Pin |
|----|------|-----|
| 1  | AISI 316L Steel | AISI 316L Steel |
| 2  | UHMWPE Polyethylene | UHMWPE Polyethylene |
| 3  | AISI 316L Steel | Torlon 4203L |
| 4  | Torlon 4203L | CoCr alloy |
| 5  | PEEK 450G | Torlon 4203L |
| 6  | UHMWPE Polyethylene | Torlon 4203L |
| 7  | Torlon 4203L | Cr PH17-4 Steel |
| 8  | Rexolite 1422 | CoCr alloy |
| 9  | PEEK 450G | CoCr alloy |
| 10 | PEEK CF (30%) | CoCr alloy |
| 11 | PEEK CA (30%) | CoCr alloy |
| 12 | UHMWPE Polyethylene | CoCr alloy |
| 13 | CoCr alloy | UHMWPE Polyethylene |
| 14 | UHMWPE Polyethylene | Cr PH17-4 Steel |

The selection of the couplings to be tested took place adaptively as the tests went on, taking into consideration the results obtained so far.

In particular, initially the coupling currently most widely used, i.e. that between polyethylene and CoCr alloy, was tested.

Then, the polyethylene was replaced by materials exhibiting a lower debris emission, and in particular first by torlon and then by natural PEEK. Subsequently, always pin material being equal, a Carbon fibre—reinforced PEEK disc was used, in order to maintain the wettability properties of the preceding case, yet obtaining a higher mechanical strength.

Then, the CoCr alloy was substituted by a more cost-effective and high-strength Chromium steel.

Afterwards, always with a Chromium steel pin, a tornon disc was used, thereby attaining a coupling between two materials having a high and comparable hardness. The other couplings of Table 1 were selected in order to perfect the conclusions derived from the results obtained by the preceding couplings.

The following Table 2 specifies the chemical composition of the metallic materials used in the tests.

TABLE 2

CHEMICAL COMPOSITION OF THE TESTED METALLIC MATERIALS
(% of weight)

| Element | AISI316L Steel | PH 17-4 Steel | CoCr alloy |
|---------|----------------|---------------|------------|
| Fe | 65.0 | 73.0 | <0.75 |
| C  | <0.03 | 0.07 | <0.35 |
| Cu | <0.05 | 3.0 ÷ 5.0 | — |
| Cr | 17.0 ÷ 20.0 | 15.0 ÷ 17.5 | 27.0 ÷ 30.0 |
| Mn | <2.0 | 1.0 | <1.0 |
| Mo | 2.25 ÷ 3.50 | 0.50 | 5.0 ÷ 7.0 |
| Ni | 13.0 ÷ 16.0 | 3.0 ÷ 5.0 | <1.0 |
| P  | <0.025 | 0.04 | — |
| S  | <0.01 | 0.03 | — |
| Si | <0.75 | 1.0 | <1.0 |
| Nb/Ta | — | 0.45 | — |

Instead, as far as the polymeric materials are concerned, the main properties thereof are summarized in the following Table 3.

TABLE 3

MAIN PROPERTIES OF THE TESTED POLYMERIC MATERIALS

| | |
|---|---|
| PEEK 450 G | Natural peek (Polyether-ether-ketone), thermoplastic polymer having high resistance to sliding wear. |
| PEEK CF (30%) | Polyether-ether-ketone reinforced by 30% thin monodirectional carbon fibres |
| PEEK CA (30%) | Polyether-ether-ketone reinforced by short, randomly oriented Carbon fibres. |
| Rexolite 1422 | Styrene copolymer, hard thermoplastic resin having optimal insulating properties. |
| Torlon 4203L | Polyamide-imide, thermoplastic polymer reinforced by $TiO_2$ (3%) and fluorocarbon (0.5%), having optimal fatigue wear resistance at high-frequency cycles and with temperatures greater than 200° C. |
| UHMWPE Polyethylene | High - molecular weight thermoplastic polymer of ethylene, having low friction in pure sliding contacts and apt to attenuate pulse forces, yet producing a high amount of debris. |

The following Table 4 summarizes the main physical and mechanical properties of the tested materials as compared to those of the femur.

TABLE 4

PHYSICAL AND MECHANICAL PROPERTIES OF TESTED MATERIALS

| | Density (g/cm³) | Ultimate strength (MPa) | Yield strength (MPa) | Modulus of elasticity (GPa) | Ultimate elongation (%) | Hardness |
|---|---|---|---|---|---|---|
| Femur | 2.0 | 130 | — | 17 | 3 | — |
| AISI 316L steel | 8.0 | 550 | 240 | 190 | 55 | 170 (HV) |
| Cr PH 17-4 Steel | 7.8 | 1070 | 1000 | 197 | 12 | 385 (HV) |
| CoCr alloy | 8.1 | 691 | 476 | 195 | 50 | 348 (HV) |
| Rexolite 1422 | 1.05 | 48 | 27 | — | — | — |
| PEEK 450 G | 1.3 | 97 | — | 13 | 60 | 99 (HRm) |
| PEEK CF (30%) | 1.4 | 221 | — | 12 | 1 | 97 (HRm) |
| PEEK CA (30%) | 1.41 | 130 | — | 8 | 5 | 102 (HRm) |

TABLE 4-continued

PHYSICAL AND MECHANICAL
PROPERTIES OF TESTED MATERIALS

|  | Density (g/cm³) | Ultimate strength (MPa) | Yield strength (MPa) | Modulus of elasticity (GPa) | Ultimate elongation (%) | Hardness |
|---|---|---|---|---|---|---|
| Torlon 4203L | 1.41 | 190 | — | 4 | 15 | 120 (HRm) |
| UHMWPE Polyethylene | 0.95 | 30 | — | 1 | 200 | — |

Testing Method

For each of the couplings reported in Table 1, the tribological behaviour under two different working conditions, e.g. under dry and aqueous lubrication condition, was investigated. For each condition, where it was deemed necessary to confirm the obtained results, more than one test was carried out. However, hereinafter at all times reference will be made to a reference testing for each of said working conditions and for each coupling.

Preliminary to the battery of tests, the magnitude of the load to be applied onto the pin was selected according to the criteria reported below. Moreover, prior to each test the wear surfaces of the disc and of the pin underwent lapping and subsequent roughness verification, the wettability of the materials was measured and the biocompatibility thereof was verified. Also each of these preliminary steps is detailed hereinafter.

Selection of the Test Load

It is known that, in a healthy subject, the load which acts onto the femoral head during the performance of biomechanically demanding motor tasks, like e.g. running or climbing/descending stairs, can exceed the body weight of up to seven-fold.

In presence of a satisfactory articular congruence, such load distributes uniformly over a wide articular surface. On the contrary, in presence of pathological conditions, like e.g. a valgus hip or a partial dislocation of the femoral head, the load per surface unit can be much higher than that exerted under physiological conditions, due to a defective contact between the articular surfaces. Hence, in order to attain a likely simulation of the load conditions of the articulation, the load per surface unit to be applied at the pin-disc contact was computed as follows.

The current femoral heads made of CoCr alloy have a spherical surface of a radium equal to 1.4 cm, and therefore a total outer surface equal to about 24.7 cm². The actual surface which supports an equally distributed load is equal to 30% of the total one, i.e. it has an extension equal to about 7.5 cm². Taking into account that a person's average body weight is equal to 70 kg and that for some specific movements the load applied is seven-fold the body weight, a maximum total load of about 500 kg has been hypothesized, and hence a load per surface unit equal to about 0.67 kg/mm². Selecting a safety factor equal to about three, a concentrated load of 20 N was applied onto the pin.

The allowance attained by applying said safety factor also enabled to extend the applicability of the results obtained to time periods longer than the actual testing time.

Preparation of the Wear Surface

Prior to the test, a surface lapping was carried out onto the test pieces, up to values of the Ra coefficient comprised in a range of about 0.08+0.03 μm.

The following Table 5 reports the roughness values measured at the end of the lapping for all the materials.

TABLE 5

ROUGHNESS OF WEAR SURFACES

| Material | Roughness Ra (μm) |
|---|---|
| AISI 316L Steel | 0.03 |
| Cr PH 17-4 Steel | 0.03 |
| CoCr alloy | 0.05 |
| Rexolite 1422 | 0.07 |
| PEEK 450G | 0.06 |
| PEEK CF (30%) | 0.05 |
| PEEK CA (30%) | 0.04 |
| Torlon 4203L | 0.07 |
| UHMWPE Polyethylene | 0.08 |

Moreover, prior to being mounted onto the tribometer, the pins and the discs underwent a thorough cleansing in acetone solvent.

Measurement of the Material Wettability

With reference to FIG. 1, the wettability of each material was measured according to known modes, and in particular considering the angle of contact of a drop resting onto a flat surface of the material itself. More precisely, the angle θ formed by the flat material surface with the tangent to the drop side surface at a point of contact, said side surface being assumed to have a substantially spherical contour, was measured. This angle θ was computed by the formula:

$$\theta = 2\ \mathrm{arc}tg\left(2\frac{h}{d}\right),$$

where h and d are the height and the base diameter, respectively, of the drop, i.e. the diameter of the surface of contact with the material. In order to carry out the measuring, each material was photographed, under the same angle, with a water drop deposited thereon.

The measured angle values are reported in the following Table 6.

TABLE 6

ANGLE OF WETTABILITY OF TESTED MATERIALS

| Material | Wettability θ (deg) |
|---|---|
| Cr PH 17-4 Steel | 45 |
| CoCr alloy | 47 |
| Torlon 4203L | 55 |
| AISI 316L Steel | 57 |
| Rexolite 1422 | 60 |
| PEEK 450G | 64 |
| PEEK CF (30%) | 64 |
| PEEK CA (30%) | 64 |
| UHMWPE Polyethylene | 65 |

In light of the obtained data, there were classified as wettable, or hydrophilic, the Cr PH 17-4 Steel and the CoCr alloy, as of average wettability the Torlon 4203L and the AISI 316L Steel, and as not-wettable, or hydrophobic, the materials Rexolite 1422, PEEK 450G, PEEK CF (30%), PEEK CA (30%) and UHMWPE Polyethylene.

It is understood that the material wettability could also be measured by alternative methods.

Biocompatibility in a Biological Environment

As it is known, a first biocompatibility analysis for the materials for articular prostheses is that associated with the corrosion of the metals they are made of. In fact, localized corrosion could result, combined with mechanical fatigue, in an early breaking of the femoral stem, and the generation of metal ions could determine harmful effects in the host organism, at a local as well as at a systemic level. In patients carrying metal prostheses, these values are magnified, and such magnified values remain chronically. Moreover, abnormal metal concentrations are found in the tissues of such patients, both locally, near to the prosthesis, and in remote regions.

Some metals, e.g. Vanadium, can be more dangerous as they exhibited cytotoxic properties in vitro. In general, however, the effects of high quantities of metal in the human body are not entirely known, although it is known that some metals magnify certain metabolic and catabolic processes, for example cobalt magnifies protein synthesis and chromium magnifies the regulation of the metabolic energy. Moreover, metals, combining with some proteins, can activate the immune system response, inducing an allergy to metal.

Therefore, for the tests of the present invention materials chemically compliant to the above were selected. In particular, Rexolite, Torlon and Polyethylene all belong to the class of materials for biomedical use, whereas PEEK has no elements harmful to the biological environment as it incorporates the etheric group —C—O—C—, an R-0-R-type volatile chemical compound wherein R is an hydrocarbon radical, and an organic compound containing the characteristic =CO group.

As regards the selected metallic materials, CoCr alloy, PH 17-4 Steel and AISI 316L Steel, these do not comprise chemical substances harmful to the human body.

During each of the tests carried out, the tribometer has provided the time pattern of the friction coefficient between the pin and the disc at the increase of the number of cycles, evaluated by detecting the tangential contact force.

Moreover, always during each test, the tribometer has provided the time pattern of a wear parameter, assessed in millimeters and evaluated as the lowering of the pin onto the disc.

For a better qualitative and quantitative assessment of the overall wear of the materials of the coupling, at the start and at the end of each test the pin and the disc have been weighted separately. Moreover, at the end of each test, the surfaces of the pin and of the disc have been analyzed and photographed at the Scanning Electron Microscope (hereinafter indicated with the acronym SEM).

For clarity's sake, the operative conditions common to all tests are summarized in the following Table 7.

TABLE 7

OPERATIVE CONDITIONS DURING THE TESTS

| | |
|---|---|
| Angular velocity | 100 cycles/min |
| Linear velocity | 0.18 m/min, mean radius of track 1.7 cm |
| Normal load applied | 20 N |
| Surface finishing | Polishing and lapping |
| Cleansing solvent | Acetone $CO(CH_3)_2$ |
| Lubrication* | Continuous drop addition |
| Lubricant* | Demineralized water |
| Test duration | 10.000 cycles = 1 km |
| Environmental conditions | Measuring temperature and relative humidity |
| Quantities measured during the test | Tangential force (measured every 1000 cycles) Wear (mm) (measured every 1000 cycles) |

*If present

As the general modes of the pin-on-disc-type testing and the apparatuses therefor are well-known to those skilled in the art, a further description thereof will be omitted.

Test Results

The following Table 8 reports the final wear values and the final friction coefficient of the tested couplings under dry and under aqueous lubrication conditions, and the difference ($\Delta\theta$) between the angles of wettability of the materials of each coupling.

TABLE 8

CHART OF RESULTS I

| | Coupling | | Friction coefficient (at 10000 cycles) | | Wear (at 10000 cycles) (mm) | | $\Delta\theta$ |
|---|---|---|---|---|---|---|---|
| | Disc | Pin | Dry | Water | Dry | Water | (deg) |
| 1. | AISI 316L Steel | AISI 316L Steel | Seizure | Seizure | Seizure | Seizure | 0 |
| 2. | UHMWPE Polyethylene | UHMWPE Polyethylene | 0.6 | Interrupted (*) | 0.025 | Interrupted (*) | 0 |
| 3. | AISI 316L Steel | Torlon 4203L | 0.65 | 0.23 | 0.043 | 0.07 | 2 |
| 4. | Torlon 4203L | CoCr alloy | 0.3 | 0.35 | 0.005 | 0 | 8 |
| 5. | PEEK 450G | Torlon 4203L | 0.25 | 0.5 | 0.0 | 0.004 | 9 |
| 6. | UHMWPE Polyethylene | Torlon 4203L | 0.22 | 0.15 | 0 | 0 | 10 |
| 7. | Torlon 4203L | Cr PH17-4 steel | 0.4 | 0.1 | 0 | 0.003 | 10 |
| 8. | Rexolite 1422 | CoCr alloy | 0.3 | 0.1 | 0.08 | 0.03 | 13 |
| 9. | PEEK 450G | CoCr alloy | 0.35 | 0.2 | −0.035 | 0.013 | 17 |
| 10. | PEEK CF | CoCr alloy | 0.15 | 0.05 | 0 | 0 | 17 |
| 11. | PEEK CA | CoCr alloy | 0.25 | 0.15 | 0.05 | 0 | 17 |
| 12. | Polyethylene | CoCr alloy | 0.2 | 0.05 | 0 | 0.035 | 18 |
| 13. | CoCr alloy (**) | UHMWPE Polyethylene | 0.2 | 0.05 | 0.035 | 0.065 | 18 |
| 14. | UHMWPE Polyethylene | Cr PH17-4 Steel | 0.22 | 0.05 | 0.02 | 0.015 | 20 |

(*) Test interrupted due to incipient seizure.

(**) Additional test aimed at checking system geometry.

The following Table 9 reports weight variation values (ΔP) values before and after the test for the pin and for the disc, as well as the width of the track on the disc for the couplings evaluated ex post as the most relevant ones.

over debris had a much smaller size. Further, it was found that the torlon particles, being extremely hard, had damaged the CoCr pin and that, vice versa, tears typical of the wear of a polymer material appeared onto the torlon track.

TABLE 9

CHART OF RESULTS II

| Coupling (materials per weighing) | | dry ΔP (g) | | Aqueous ΔP (g) | | Track width (mm) | | Δθ | Debris of |
|---|---|---|---|---|---|---|---|---|---|
| Disc | Pin | Disc | Pin | Disc | Pin | dry | water | (deg) | aqueous test |
| 4 Torlon 4203L | CoCr alloy | 0.0011 | 0.0002 | −0.0015 | 0.0006 | 0.6 | 0.6 | 8 | scarce debris |
| 5 Peek 450G | Torlon 4203L | 0.0035 | 0.0 | −0.0185 | 0.0 | 0.6 | 0.9 | 9 | a lot of debris |
| 6 UHMWPE Polyethylene | Torlon 4203L | 0.0004 | −0.0002 | 0.0003 | −0.0009 | 1.6 | 1.2 | 10 | a lot of debris |
| 7 Torlon 4203L | Cr PH17-4 steel | 0.0009 | 0.0 | −0.0120 | 0.0 | 0.5 | 0.5 | 10 | scarce debris |
| 9 PEEK 450G | CoCr alloy | 0.0017 | 0.0 | −0.0014 | −0.0002 | 1.0 | 0.9 | 17 | little debris |
| 10 PEEK CF | CoCr alloy | 0.0001 | 0.0 | 0.0002 | 0.0 | 0.6 | 0.2 | 17 | absence of debris |
| 11 PEEK CA | CoCr alloy | 0.0036 | 0.0014 | 0.0040 | 0.0003 | 0.6 | 0.2 | 17 | absence of debris |
| 12 Polietilene | CoCr alloy | −0.0002 | 0.0005 | −0.0004 | 0.0007 | 1.5 | 1.0 | 18 | a lot of debris |
| 14 UHMWPE Polyethylene | Cr PH17-4 steel | −0.0013 | 0.0 | −0.0005 | −0.0002 | 1.6 | 0.6 | 20 | little debris |

Coupling 12—Pin of CoCr Alloy, Disc of UHMWPE Polyethylene

Figure 2A:
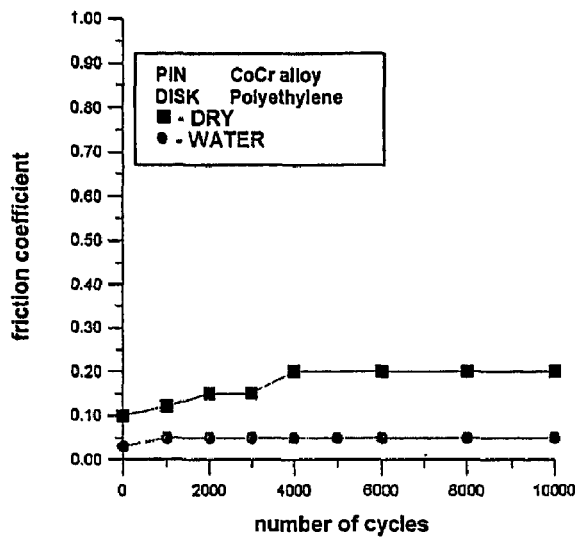
FIGS. 2A, 4A, 6A, 8A, 10A, 12A, 14A, 16A, 18A and 19A each show a graph of the pattern of the friction coefficient between prosthetic materials, during a respective experimental test.
Figure 2B:
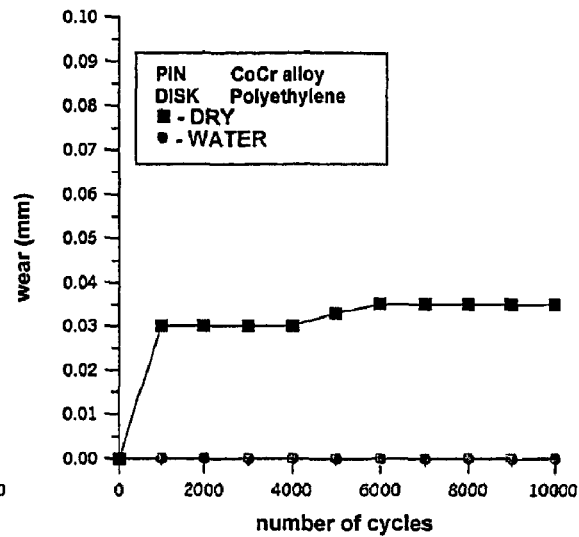
FIGS. 2B, 4B, 6B, 8B, 10B, 12B, 14B, 16B, 18B and 19B each show a graph of the pattern of a wear parameter related to a certain coupling between prosthetic materials, during a respective experimental test.
Figure 3A:
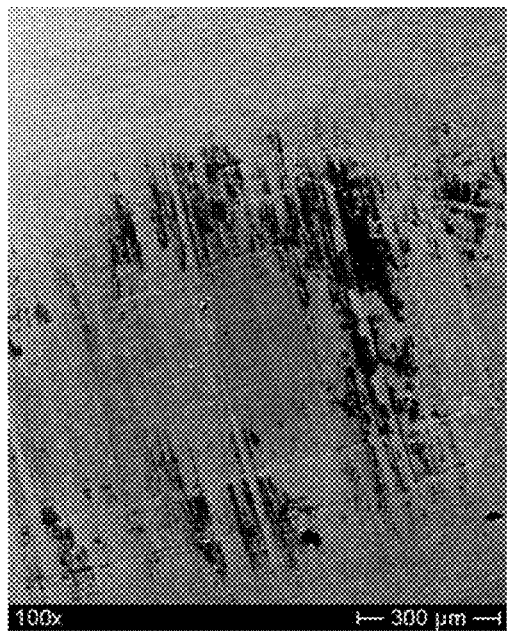
FIGS. 3A to 3D, 5A and 5B, 7A and 7B, 9A and 9B, 11A to 11D, 13A to 13C, 15A to 15D and 17A to 17D each show a photo of a respective test piece taken by the scanning electron microscope.
Figure 3B:

FIGS. 2A and 2B show each an experimental graph, depicting the pattern of the friction coefficient and that of wear during the dry and the aqueous test, respectively. FIGS. 3A e 3C show each a SEM photo of the pin at the end of the dry and of the aqueous test, respectively. FIGS. 3B and 3D show likewise photos for the disc. With reference to FIGS. 3A and 3B, in the dry test the SEM photos have highlighted a deflection of the track, which also exhibited tears typical of the adhesive wear of plastic materials and was covered by a lot of debris. Moreover, the pin appeared covered with polyethylene. This deflection of the track and the fact that the latter was filled up with debris compensated for the lowering of the pin onto the disc, thereby remarkably altering the reading of the wear, for which in Table 8 a void value is in fact reported. However, the rather high friction coefficient (0.2, as reported in Table 8) hints at the actual outcome of the test. Moreover, as reported in Table 9, in this case the wear by weight loss of the disc was found to be negative, confirming an increase in weight due to the presence of debris.

Figure 3C:
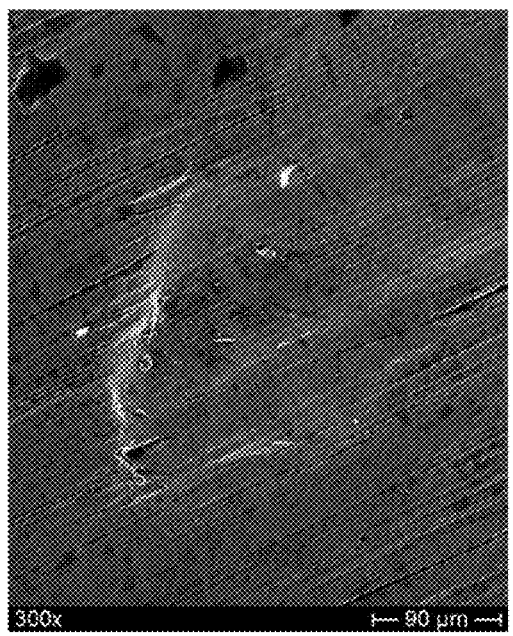
Figure 3D:

With reference to FIGS. 3C and 3D, the SEM photos showed that at the end of the aqueous test the pin surface was slightly etched, with some debris on its surface, whereas the disc track was free from debris. It has also been found that the latter positioned far from the track itself. This fact confirmed the cleansing action of water. As reported in Table 9, always in the aqueous test, the track onto the disc had a width lower than that related to the dry test. Though the difference in the angle of wettability is very high (18 deg), this coupling is affected by the marked chip-forming attitude of polyethylene.

Coupling 4—Pin of CoCr Alloy Disc of Torlon

Figure 4A:
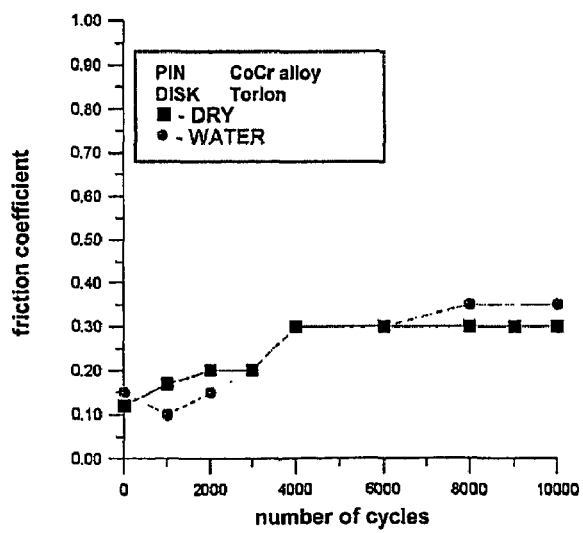
Figure 4B:
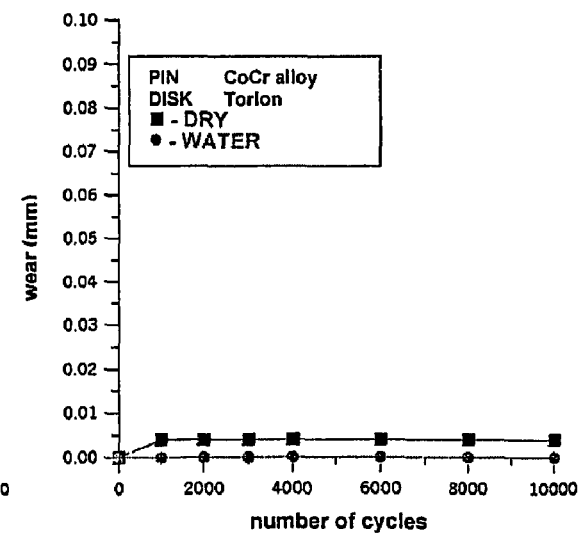
Figure 5A:
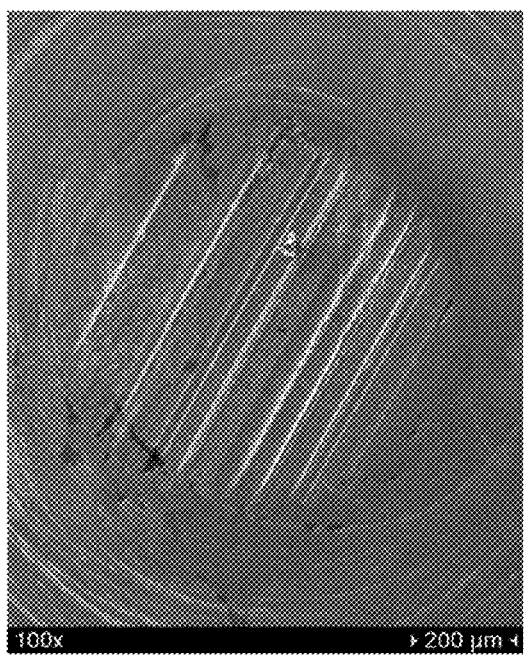
Figure 5B:
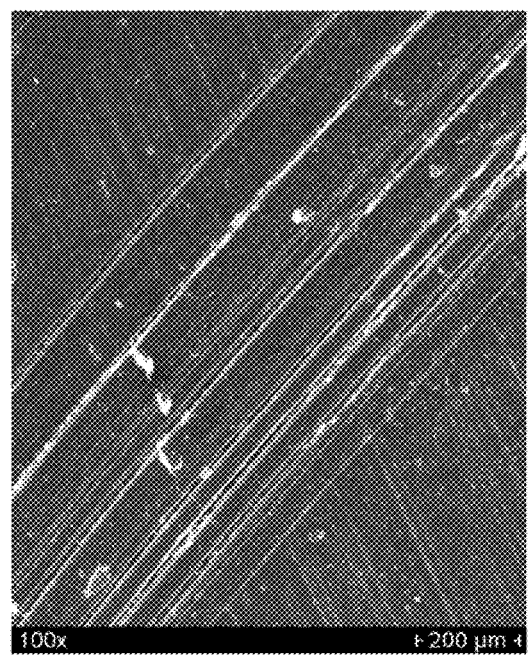

FIGS. 4A and 4B show each an experimental graph depicting the pattern of the friction coefficient and that of wear during the dry and the aqueous test, respectively. FIGS. 5A and 5B show each a SEM photo related to the pin and to the disc, respectively, at the end of the aqueous test.

SEM analysis of the pin and of the disc at the end of the dry test showed a remarkably reduced quantity of debris with respect to the preceding case of polyethylene disc, and more- Also the SEM analysis of the test pieces at the end of the aqueous test highlighted a scarce production of debris. The scarce debris of the pin and of disc were however very hard and had caused a marked abrasion wear onto the track. In corroboration of this, in this case, as reported in Table 8, the friction coefficient was greater than that of the corresponding dry test. Both the materials exhibit a hydrophobic behaviour, hence no supporting meatus ensues.

Coupling 9—Pin of CoCr Alloy Disc of PEEK 450G

Figure 6A:
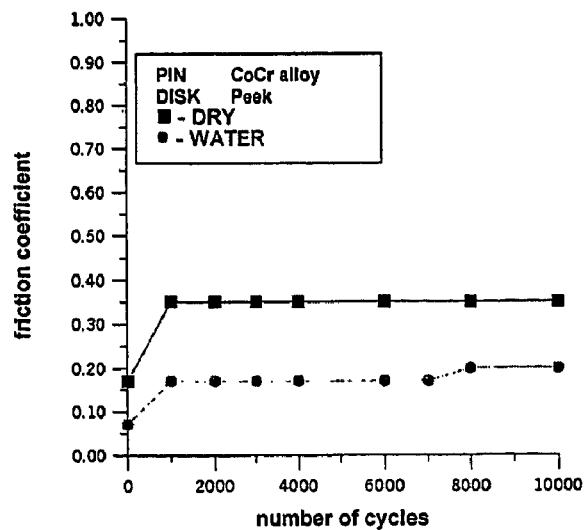
Figure 6B:
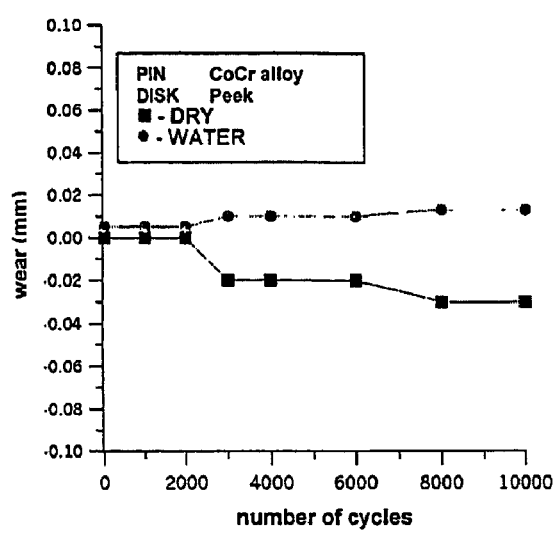
Figure 7A:
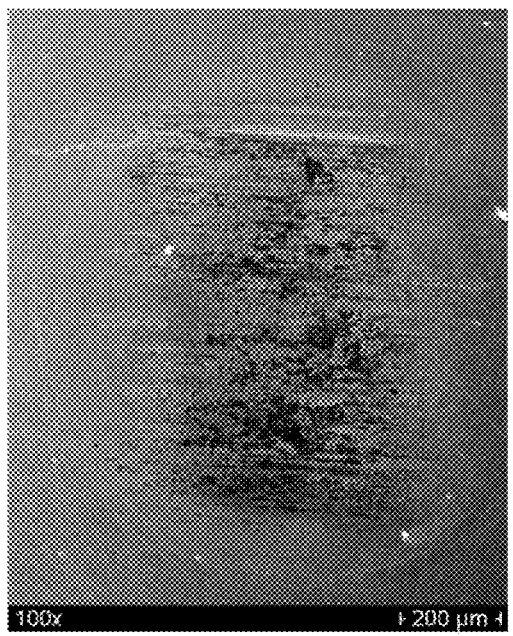
Figure 7B:
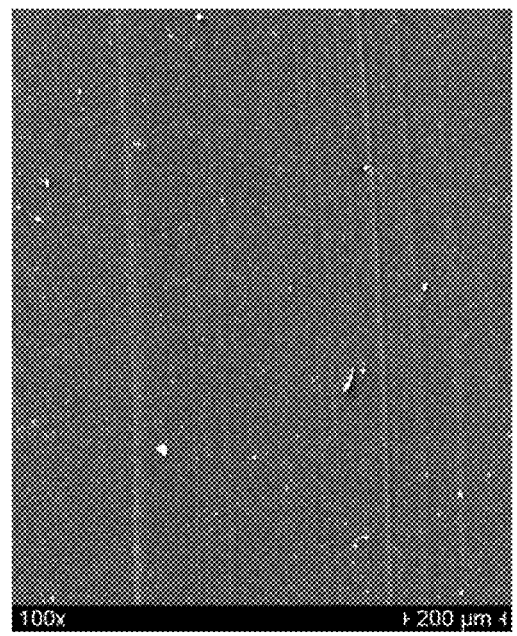

FIGS. 6A e 6B show each an experimental graph depicting the pattern of the friction coefficient and that of wear during the dry and the aqueous test, respectively. FIGS. 7A and 7B show each a SEM photo of the pin at the end of the dry test and of the disc at the end of the aqueous test, respectively.

With reference to FIG. 7A, the SEM analysis of the test pieces at the end of the dry test highlighted the presence of debris adhered onto the pin. This event altered the measuring of wear, which in fact yielded void values, as it is apparent from Table 8. In this case as well, the high values of the friction coefficient, always reported in Table 8, hint at the actual outcome of the test.

In the aqueous test a friction coefficient lower than that of the dry test and a wear near to nil were attained. The debris cleansing action by the water and the lubricating action due to the marked difference in wettability are apparent.

Coupling 10—Pin of CoCr Alloy, Disc of PEEK CF

Figure 8A:
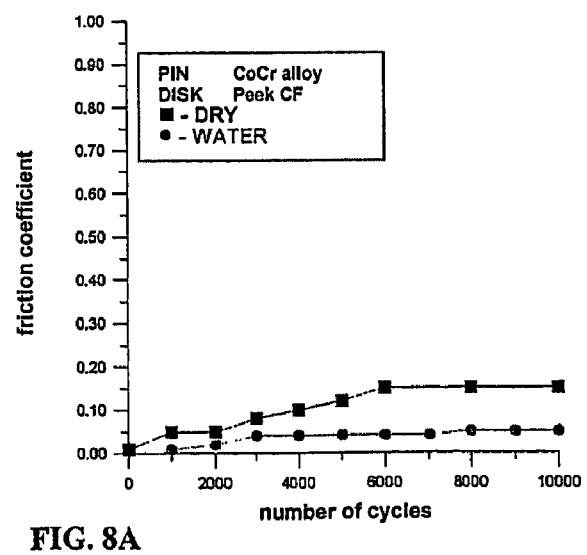
Figure 8B:
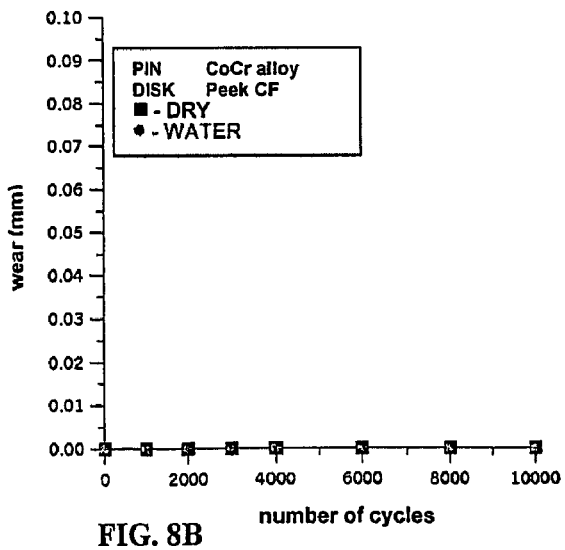
Figures 9A, 9B:
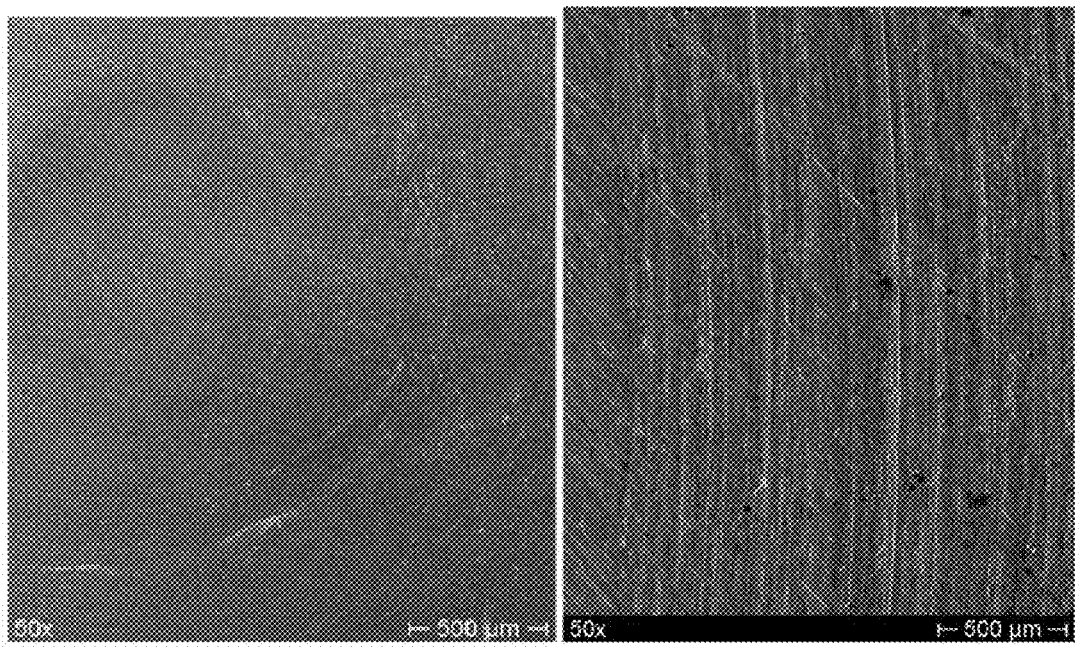

FIGS. 8A and 8B show each an experimental graph depicting the pattern of the friction coefficient and that of wear during the dry and the aqueous test, respectively. FIGS. 9A and 9B show each a SEM photo of the pin and of the disc, respectively, at the end of the aqueous test.

The aqueous test was among the most interesting to tribological ends. In fact, it highlighted, as it is shown in the SEM photo of FIGS. 9A and 9B, the almost total absence of debris and a remarkably low friction coefficient, as it can be appreciated from Tables 8 and 9 and from FIGS. 8A and 8B.

In particular, said SEM photos highlight that, after 10.000 cycles, the pin surface had no wear and the disc track was almost null. Intact material fibres are noted.

Coupling 11—Pin of CoCr Alloy, Disc of PEEK CA

Figure 10A:
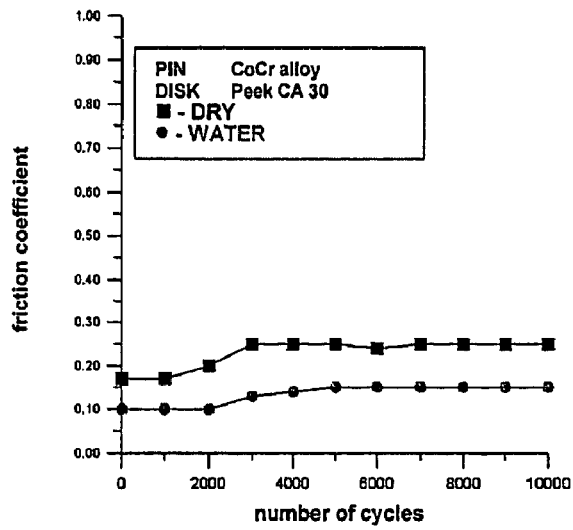
Figure 10B:
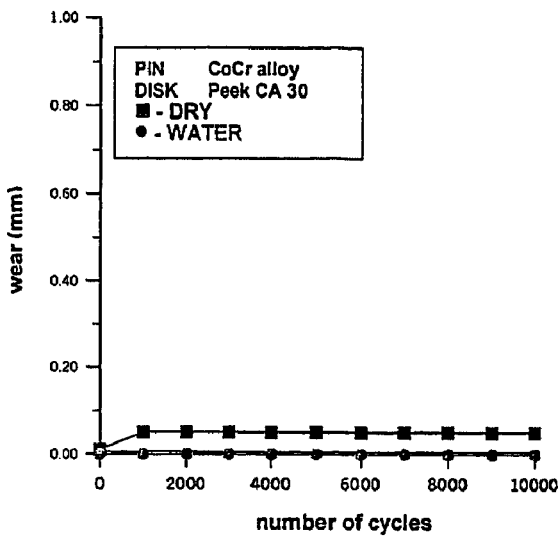
Figure 11A:
Figure 11B:
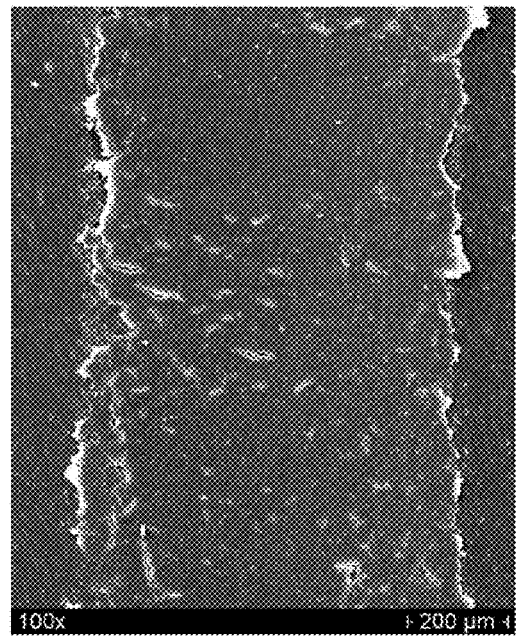
Figure 11C:
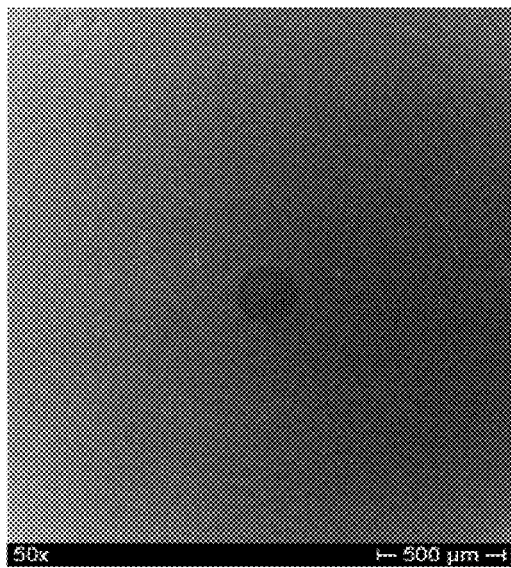
Figure 11D:
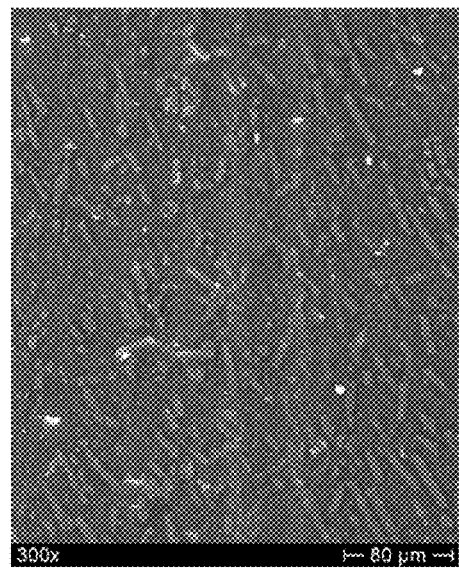

FIGS. 10A and 10B show each an experimental graph depicting the pattern of the friction coefficient and that of wear during the dry and the aqueous test, respectively. FIGS. 11A and 11C show each a SEM photo of the pin, at the end of the dry and of the aqueous test, respectively. FIGS. 11B and 11D show likewise photos for the disc.

As it is shown also on the SEM photos reported in FIGS. 11B and 11C, the aqueous test ended with an almost total absence of debris besides a very low friction coefficient, which reached a maximum value of 0.05. In particular, after 10 000 cycles the track onto the disc was almost null.

Coupling 14—Pin of PH 17-4 Chromium Steel, Disc of Polyethylene

Figure 12A:
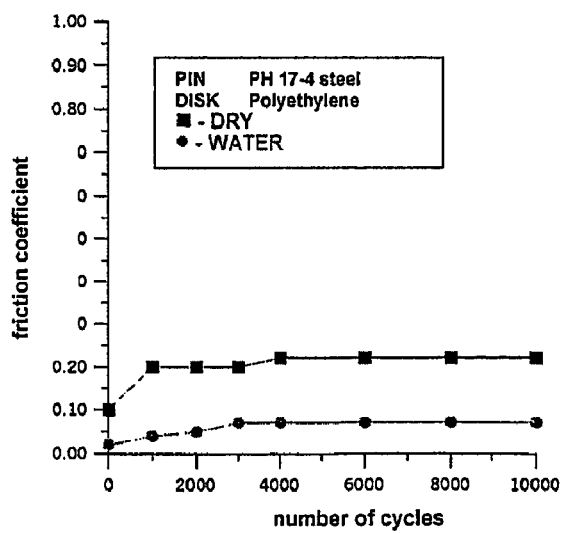
Figure 12B:
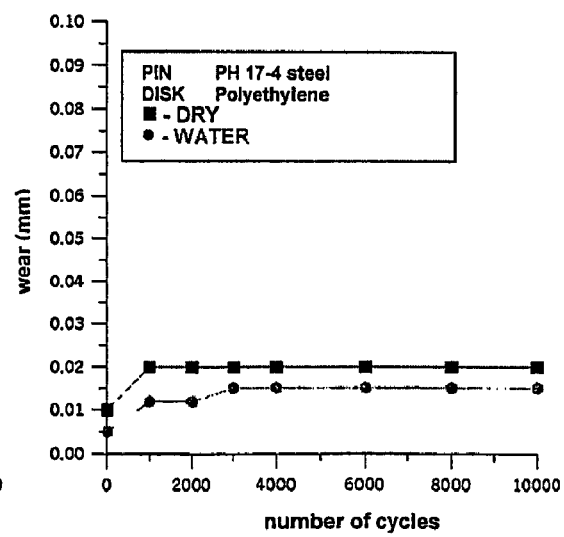
Figure 13A:
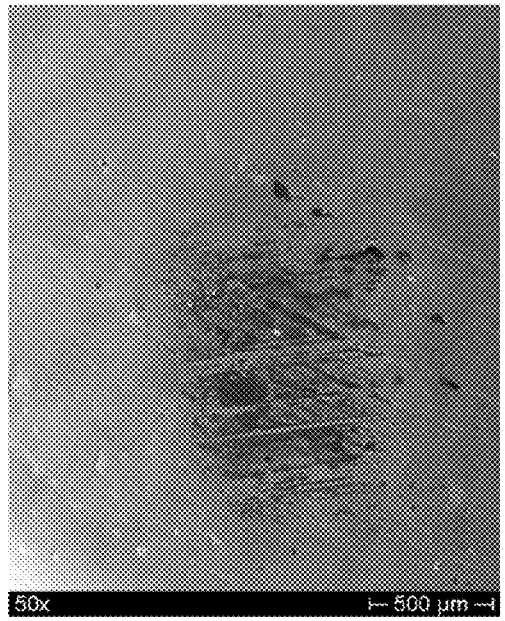
Figure 13B:
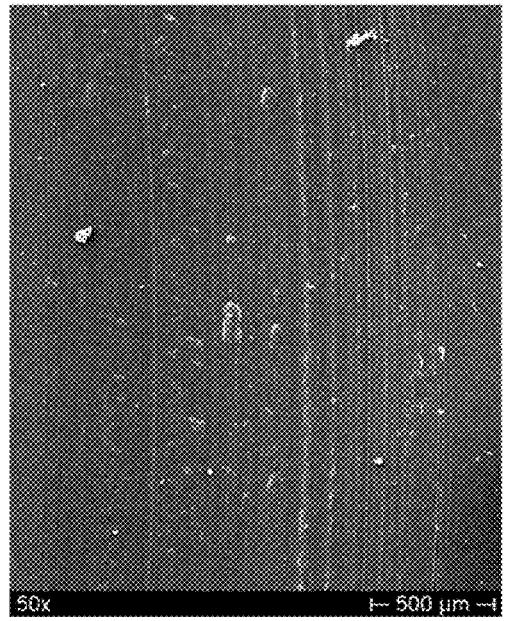
Figure 13C:
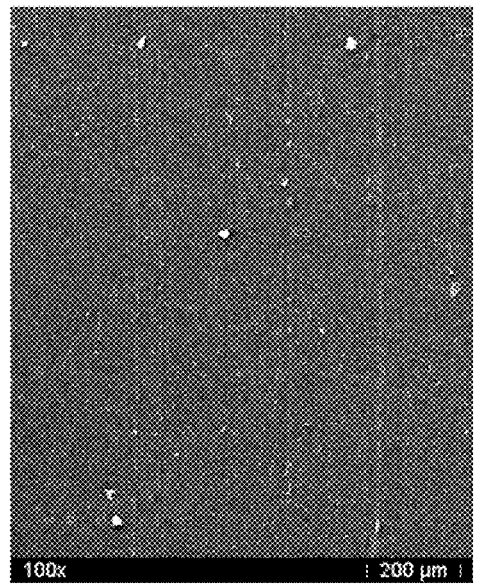

FIGS. 12A e 12B show each an experimental graph depicting the pattern of the friction coefficient and that of wear during the dry and the aqueous test, respectively. FIG. 13A shows a SEM photo of the pin at the end of the dry test. FIGS. 13B and 13C show each a SEM photo of the disc at the end of the dry and of the aqueous test, respectively.

In the dry test, wear was entirely ascribable to the polyethylene disc. In fact, the SEM analysis showed that the pin was covered with polyethylene debris and the disc track had tears typically due to the wear of a polymeric material.

As highlighted in Table 8, the aqueous test showed a low friction coefficient and a low wear. In particular, as highlighted in FIG. 13A, wear was almost null for the pin as well as for the disc, with a nearly invisible track on the latter. The quantity of debris was lower with respect to the corresponding test of the CoCr alloy-polyethylene coupling, and in particular almost null.

Coupling 7—Pin of PH 17-4 Chromium Steel, Disc of Torlon

Figure 14A:
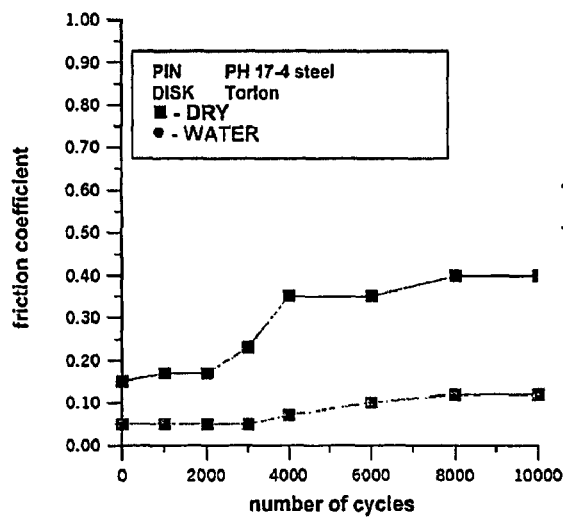
Figure 14B:
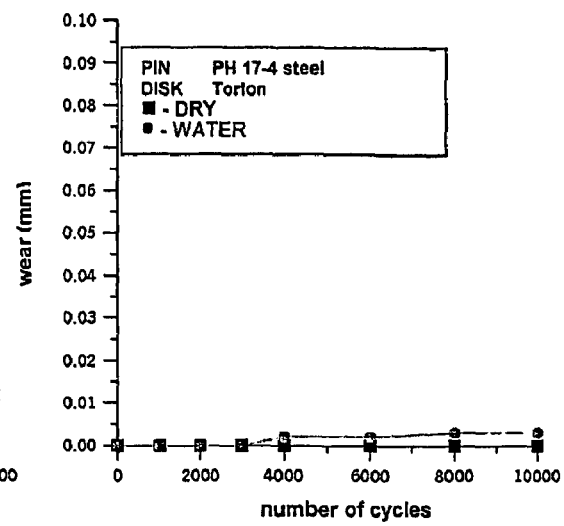
Figure 15A:
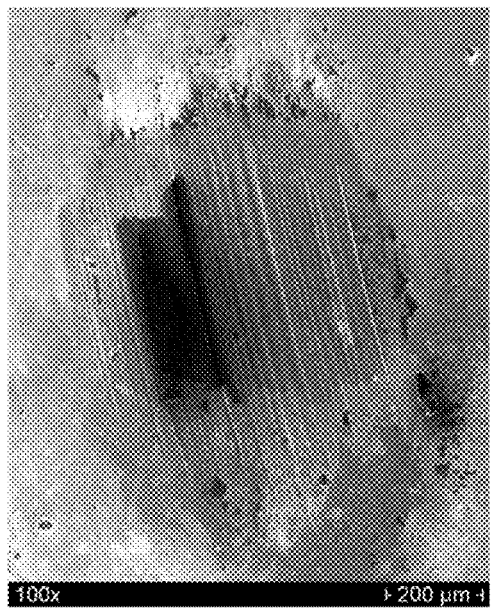
Figure 15B:
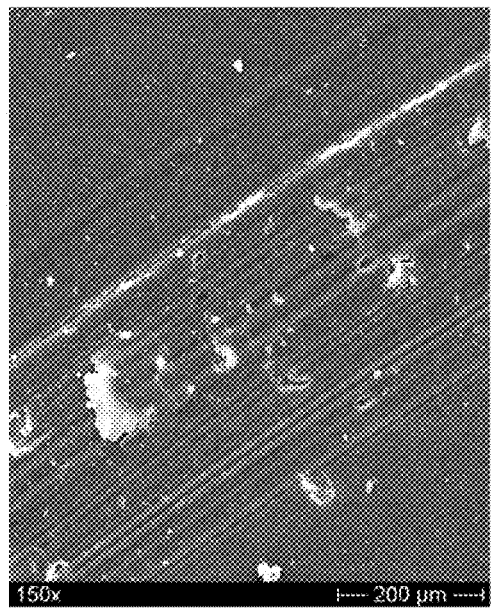
Figure 15C:
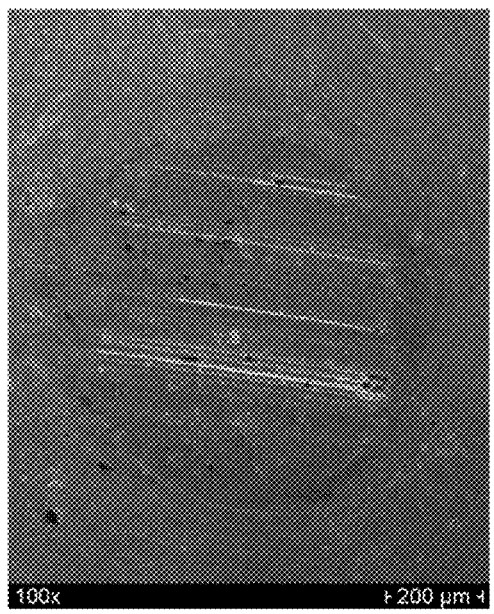
Figure 15D:
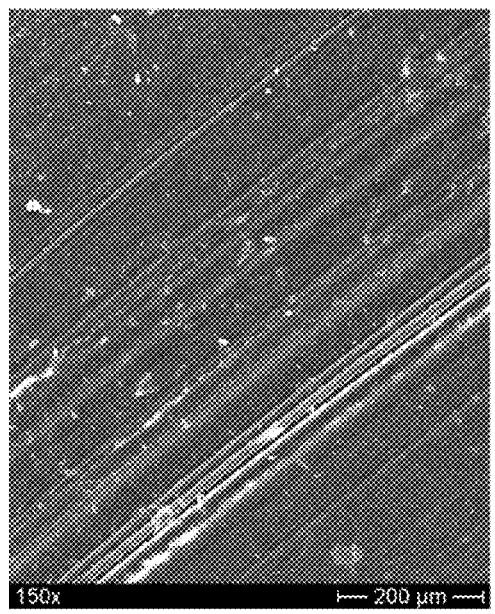

FIGS. 14A and 14B show each an experimental graph depicting the pattern of the friction coefficient and that of wear during the dry and the aqueous test, respectively. FIGS. 15A and 15C show each a SEM photo of the pin at the end of the dry and of the aqueous test, respectively. FIGS. 15B and 15D show likewise photos for the disc.

Tables 8 and 9 indicate that the dry test entailed a high friction coefficient and a low wear. However, this latter datum was altered by the presence of debris. In fact, the SEM analysis highlighted a wear of the pin surface and the presence onto the disc track of thin layers of material detached by microwelding.

In the aqueous test, the SEM analysis highlighted a slight abrasion wear of the pin and of the disc due to the presence of very hard debris of the two materials.

Coupling 6—Pin of Torlon, Disc of Polyethylene

Figure 16A:
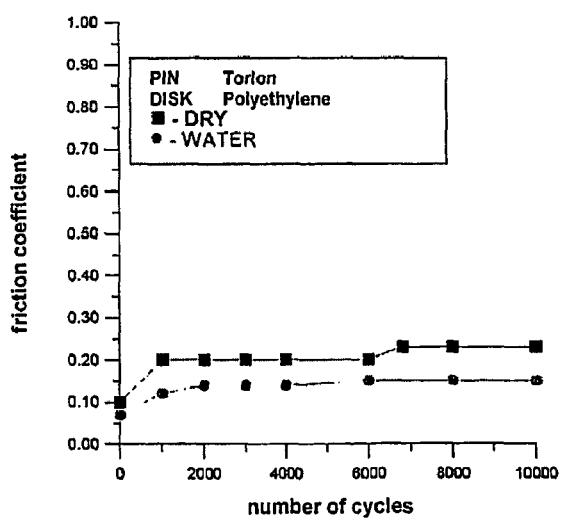
Figure 16B:
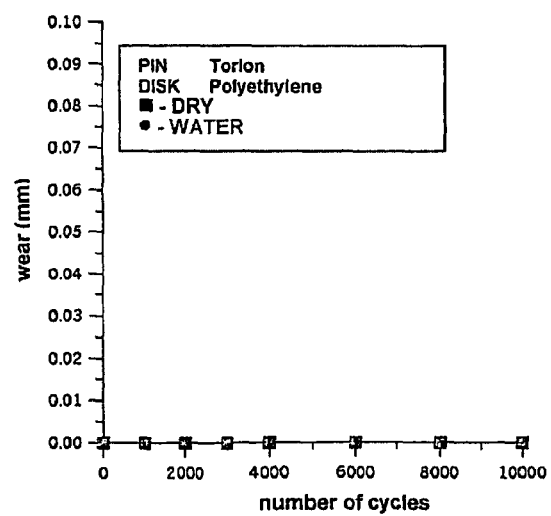
Figure 17A:
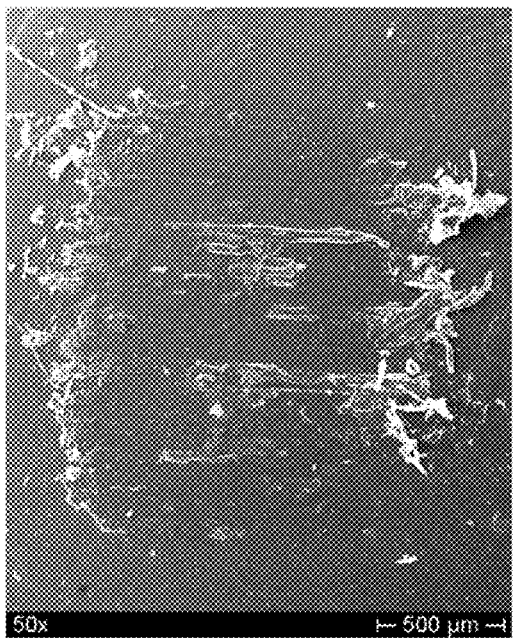
Figure 17B:
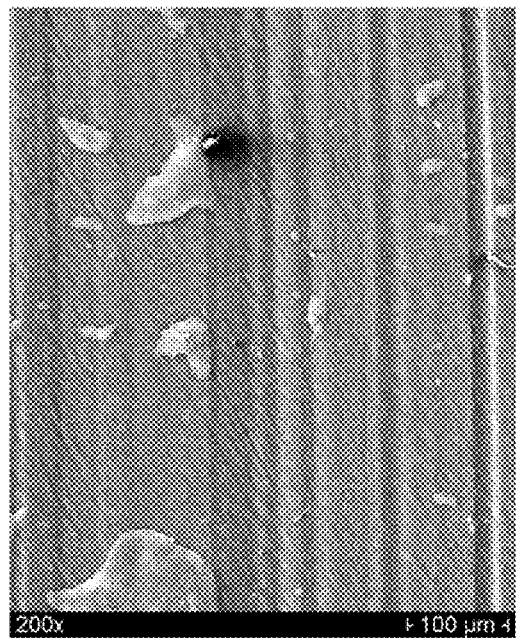
Figure 17C:
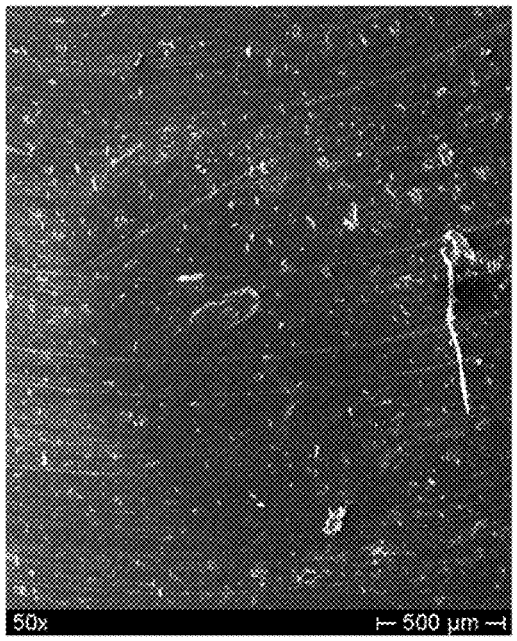
Figure 17D:
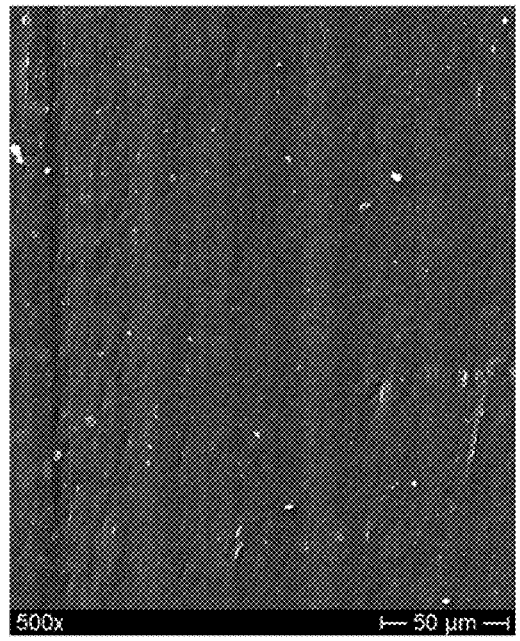

FIGS. 16A and 16B show each an experimental graph depicting the pattern of the friction coefficient and that of wear during the dry and the aqueous test, respectively. FIGS. 17A and 17C show each a SEM photo of the pin at the end of the dry and of the aqueous test, respectively. FIGS. 17B and 17D show likewise photos for the disc.

The SEM analysis at the end of the dry test highlighted that the pin exhibited no wear, but large polyethylene debris applied thereon. The disc track appeared markedly worn and full of debris.

In this case as well, the null wear value highlighted in Tables 8 and 9 is altered by the presence of the debris itself.

In the aqueous test, the debris-cleansing action of the water was highlighted.

Coupling 5—Pin of Torlon, Disc of Natural PEEK

Figure 18A:
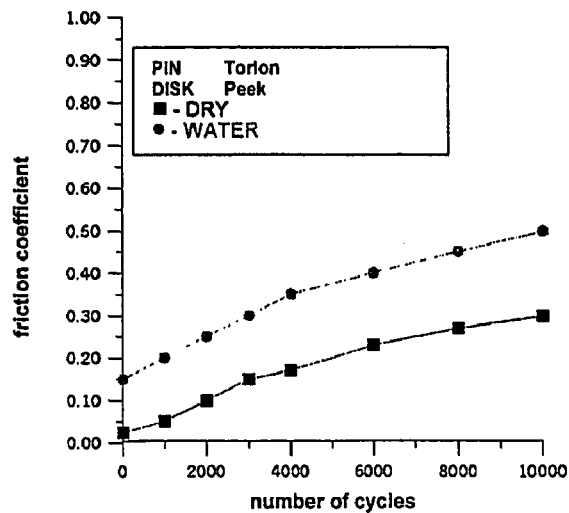
Figure 18B:
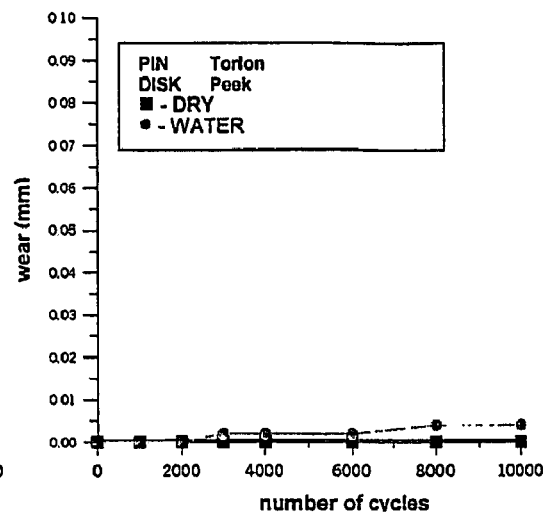

FIGS. 18A and 18B show each an experimental graph representing the pattern of the friction coefficient and that of wear during the dry and the aqueous test, respectively.

In the dry test, wear was entirely ascribable to the disc, made of a markedly chip-forming material.

As highlighted in Table 8, in the aqueous test both the friction coefficient and the wear were greater than those of the dry test. Moreover, the SEM analysis at the end of the aqueous test showed wear of the pin and of the disc with exchange of material therebetween.

Coupling 3—Pin of Torlon, disc of AISI 316L Steel

Figure 19A:
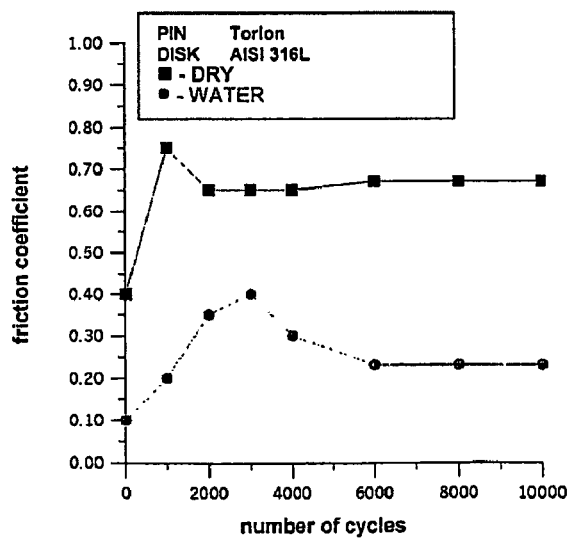
Figure 19B:
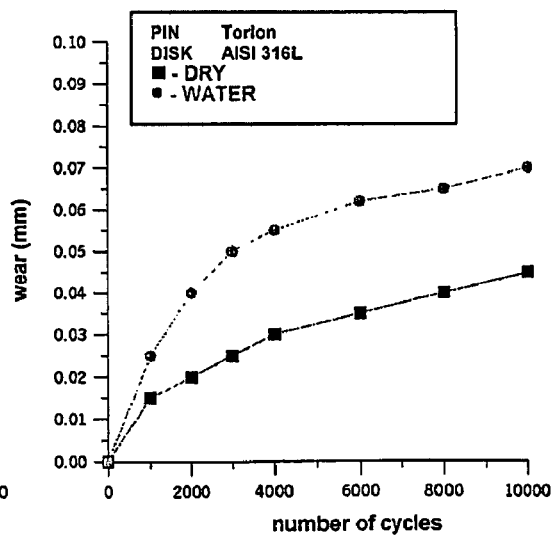

FIGS. 19A and 19B show each an experimental graph depicting the pattern of the friction coefficient and that of wear during the dry and the aqueous test, respectively. The dry test showed a very high friction coefficient and an increasing wear up to a value of 0.045 mm. Moreover, at the end of the test, there was a lot of debris both in the pin and in the disc.

The aqueous test yielded more unsatisfactory results than those of the dry one, in particular in terms of wear.

Results obtained by the above-described experimental tests have highlighted the fundamental importance of the wettability of the materials constituting the prosthetic bodies of acetabular cup and femoral head for the setting up of a permanent aqueous lubrication system therebetween. In particular, it was highlighted that the greater the difference of wettability between the material forming the acetabulum and the material forming the femoral head, the easier is the establishment of a stable supporting meatus in the coupling under aqueous lubrication. The setting up of this meatus, by determining the conditions of relative motion between the prosthetic bodies, influences also the forming of wear debris.

Said characteristic of substantially different wettability of the prosthetic bodies is anyway to be associated with further features of strength of the bodies themselves such to ensure optimal mobility conditions during use of the prosthesis. The tests carried out demonstrated that a further crucial feature is low debris production of the involved materials, herewith to be intended as scarce attitude to debris forming. The behaviour detected under the different coupling situations is sketched in FIGS. 20A, 20B and 20C.

Figure 20A:
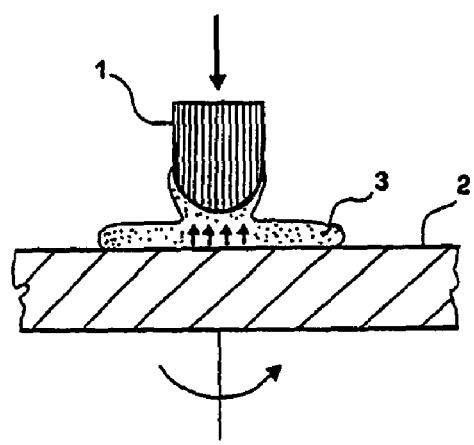
FIGS. 20A to 20C refer each to a respective lubrication condition, showing a schematic representation thereof.

With initial reference to FIG. 20A, in the case in which a pin 1 made of a hydrophilic material is coupled to a disc 2 made of a hydrophobic material, or vice versa, under aqueous lubrication with a fluid 3 a highly stable supporting meatus is formed, resulting in conditions of effective lubrication.

This is the case of the coupling between CoCr alloy and PEEK CF or PEEK CA, wherein the difference in wettability of the materials (17 deg) is magnified, and the mechanical features in terms of low debris production are excellent. This concurrence of features results in the establishment of a system of perfect lubrication, capable of withstanding (null wear and near-null friction coefficient) the drastic test conditions adopted. The better behavior of PEEK CF with respect to PEEK CA is explained by the fact that the former is formed by long and monodirectional fibres, whereas the latter, as mentioned above, has randomly oriented fibres.

Also in the CoCr alloy/PEEK CA coupling there is a concurrence between satisfactory mechanical characteristics and marked difference of the angle of wettability.

Further demonstrating the role carried out by the wettability, it is highlighted that also in the classic CoCr alloy/polyethylene coupling, which has a high difference of wettability (18 deg) between the involved materials, a satisfactory supporting meatus establishes. However, this coupling entails the problem of the marked chip-forming of polyethylene. Alike problems are associated with the CoCr alloy/PEEK 450G coupling.

Figure 20B:
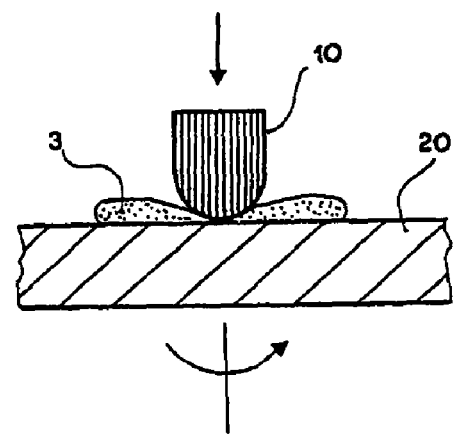

Then, with reference to FIG. 20B, it is apparent that when, instead, a pin 10 and a disc 20 made of materials of comparable wettability, and in particular both hydrophobic, are adopted, the meatus formed by fluid 3 tends to lose lift immediately, thereby determining a near-dry coupling between the pin 10 and the disc 20. This is the case of coupling a body of CoCr alloy or of natural PEEK with a body of torlon.

Figure 20C:
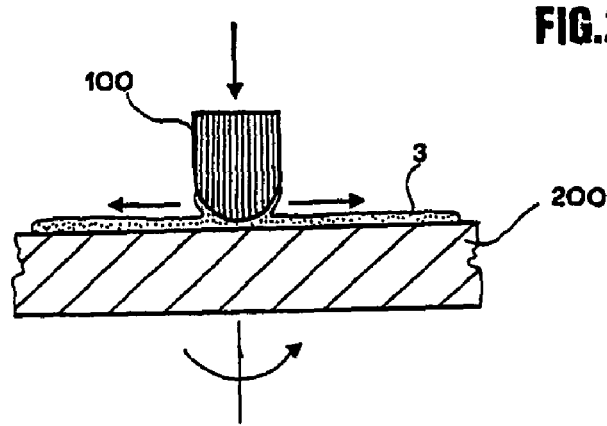

Finally, with reference to FIG. 20C, in the case when both a pin 100 and a disc 200 are made of hydrophilic materials, the fluid 3 forms an epilaminar meatus too thin to provide an effective support.

Hence, in its most general definition, the present invention provides a hip prosthesis formed by prosthetic bodies made of materials having substantially different wettability, in particular one hydrophobic and the other one hydrophilic, and low debris production.

Preferably, the hydrophilic body has an angle of wettability lower than 50 deg, and the hydrophobic body has an angle of wettability greater than 60 deg.

In light of the results of the tests carried out, in order to attain an effective supporting meatus, preferably the involved materials have a difference between the respective angles of wettability greater than 10 deg, and even more preferably equal to or greater than 15 deg.

As highlighted by the tests described above, an ideal coupling is that between CoCr alloy and PEEK reinforced by Carbon fibres, in particular PEEK CF. This entails the additional advantage that the mechanical properties in general and those of workability in particular of the involved materials are very high.

Another preferred coupling is that between CoCr alloy and PEEK CA.

The present invention further provides a designing method of hip prostheses, providing the manufacturing of prosthetic bodies having substantially different wettability.

It is understood that the condition of different wettability of the prosthetic bodies can be attained even combining, in the same prosthetic body, different materials and/or specific surface coatings.

The present invention has hereto been described with reference to preferred embodiments thereof. It is understood that there could be other embodiments belonging to the same inventive kernel, all however falling within the protective scope of the appended claims.

The invention claimed is:

1. A manufacturing method of a hip prosthesis comprising two prosthetic bodies reproducing an acetabular cup and a femoral head, respectively,
    which method provides that said prosthetic bodies have a low debris production,
    which method comprises:
        a step of selecting a CoCr alloy for manufacturing one of said bodies and PEEK reinforced with carbon fibres for manufacturing the other of said bodies;
        a step of lapping a surface of said CoCr alloy so as to obtain an angle of wettability of about 47 degrees;
        a step of lapping a surface of said PEEK reinforced with carbon fibres so as to obtain an angle of wettability of about 64 degrees,
so as to provide a large different surface wettability between said materials, one having an essentially hydrophilic and the other one an essentially hydrophobic behaviour or one a slightly hydrophilic and the other one a marked hydrophobic behaviour, or vice-versa,
said prosthetic bodies having a difference between the respective angles of wettability greater than 10 degrees.

2. The method according to claim 1, wherein said PEEK is of the type reinforced with monodirectional thin Carbon fibres.

3. The method according to claim 1, wherein said PEEK is of the type reinforced with randomly-oriented Carbon fibres.

* * * * *